United States Patent
Abramson et al.

(10) Patent No.: US 6,551,796 B1
(45) Date of Patent: Apr. 22, 2003

(54) NUCLEIC ACID ENCODING URATE TRANSPORTER AND METHODS OF USE THEREOF

(75) Inventors: Ruth G. Abramson, New York, NY (US); Edgar Leal-Pinto, New York, NY (US); Michael Lipkowitz, Kingston, NJ (US)

(73) Assignee: Mount Sinai School of Medicine, New York, NY (US)

( * ) Notice: Subject to any disclaimer, the term of this patent is extended or adjusted under 35 U.S.C. 154(b) by 0 days.

(21) Appl. No.: 09/559,023

(22) Filed: Apr. 27, 2000

Related U.S. Application Data

(63) Continuation-in-part of application No. 09/221,898, filed on Dec. 28, 1998, now abandoned.
(60) Provisional application No. 60/099,752, filed on Sep. 10, 1998, and provisional application No. 60/070,215, filed on Dec. 31, 1997.

(51) Int. Cl.[7] .......................... C12N 5/10; C12N 15/63; C12N 15/12; C12P 21/02; C07K 14/47
(52) U.S. Cl. ................. 435/69.1; 435/252.3; 435/70.3; 435/471; 435/71.1; 435/71.2; 435/325; 536/23.5; 536/24.3; 536/24.31; 530/350
(58) Field of Search .............................. 435/69.1, 70.3, 435/71.1, 71.2, 471, 325, 252.3; 536/23.5, 24.3, 24.31; 530/350

(56) References Cited

PUBLICATIONS

Sambrook et al., "——", *Molecular Cloning,* vol. 3, 1989, pp. 16.3–16.5, 16.17–16.18, 16.28–16.31.
Cunningham et al., "——", *Science,* 1989, vol. 244, pp. 1981 ——.
Leal–Pinto et al, "——", *J. Biol. Chem.,* vol. 272, 1997, pp. 617 ——.
Tureci et al., "——", *J. Biol. Chem.,* vol. 272, 1997, pp. 6416 ——.
Wada et al., "——", *J. Biol. Chem.,* vol. 272, 1997, pp. 6078 ——.
Wada et al.. "——", *J. Biol. Chem.,* vol. 99, 1997, pp. 2452 ——.
Matsumoto et al., "——", *J. Biol. Chem.,* vol. 273, 1998, pp. 16976 ——.
Leal–Pinto et al., "——", *American Society of Nephrology,* 1999 Program, Abstract A0282.
Leal–Pinto et al. "Functional Analysis and Molecular Modeling of a Cloned Urate Transporter/Channel", *J. Membrane Biol.,* vol. 169, 1999, pp. 13–27.
Lipkowitz et al., "——", *American Society of Nephrology,* 1999 Program. Abstract A0283.
Rappoport et al., "——", *American Society of Nephrology* 1999 Program, Abstract A0297.
Matsushita et al., "Requirement of Divalent Galactoside-binding Activity of Ecalectin/Galectin–9 for Eosinophil Chemoattraction", *J. Biol. Chem.,* 275, 2000, pp. 8355–8360.

*Primary Examiner*—Yvonne Eyler
*Assistant Examiner*—Fozia Hamud
(74) *Attorney, Agent, or Firm*—Baker Botts L.L.P.

(57) ABSTRACT

The present invention provides an isolated nucleic acid encoding a urate transporter, vectors comprising the nucleic acid, host cells comprising the nucleic acid, and host cells comprising the vectors. Compositions comprising the vectors and a carrier are also provided. In another embodiment, the present invention provides isolated and substantially purified urate transporter. Proteoliposomes containing substantially purified urate transporter are also provided, as well as compositions comprising the urate transporter and a carrier. The present invention further provides methods of making a urate transporter, and methods of identifying agents that inhibit or agonize the transporter.

14 Claims, 4 Drawing Sheets

```
            1                                                          50
Uat       ..MAFFSTQP PYMNPVIPFT GIIQGGLQNG LQITLQGTVH PFPNRIAVNF
Galectin5 .......... .......... .......... .......... ..........
Galectin4 MAYVPAPGYQ PTYNPTLPYK RPIPGGLSVG MSIYIQGIAK DNMRRFHVNF
Galectin7 .......... ...MSNVPHK SSLPEGIRPG TVLRIRGLVP PNASRFHVNL
Galectin8 .MLSLSNLQN IIYNPTIPYV STITEQLKPG SLIVIRGHVP KDSERFQVDF
Galectin1 .......... .......... .......... .......... ..........
Galectin2 .......... .......... .......... .......... ..........
Galectin3 .......... .......... .......... .......... ..........

51                                                         100
Uat       QTGFS...GN DIAFHFNPRF EEGGYVVCNT KQNGKWGPEE RKMQMPFQKG
Galectin5 .......... .......... .......... .......... ..........
Galectin4 AVGQD..EGA DIAFHFNPRF DGWDKVVFNT MQSGQWGKEE KKKSMPFQKG
Galectin7 LCGEE..QGS DAALHFNPRL DTSE.VVFNS KEQGSWGREE RGPGVPFQRG
Galectin8 QHGNSKLPRA DVAFHFNPRF KRSNCIVCNT LTNEKWGWEE ITHDMPFRKE
Galectin1 .......... .......... .......... .......... ..........
Galectin2 .......... .......... .......... .......... ..........
Galectin3 .......... .........M ADGFSLNDAL AGSGNPNPRG WPGAWGNQPG 101                                                        150
Uat       MPFELCFLVQ RSEFKVMVNK NFFVQYSHRV PYHLVDTISV SGCLHLSFIN
Galectin5 .......... .......... .......... .......... ..........
Galectin4 HHFELVFMVM SEHYKVVVNG TPFYEYGHRL PLQMVTHLQV DGDLELQSIN
Galectin7 QPFEVLIIAS DDGFKAVVGD AQYHHFRHRL PLARVRLVEV GGDVQLDSVR
Galectin8 KSFEIVIMVL KNKFHVAVNG KHILLYAHRI NPEKIDTLGI FGKVNISHIG
Galectin1 .......... .......... .......... .......... ..........
Galectin2 .......... .......... .......... .......... ..........
Galectin3 AGGYPGASYP GAYPGQAPPG GYPGQAPPSA YPGPTGPSAY PGPTAPGAYP
```

FIG.2A

```
              151                                                              200
      Uat     FQIQGFQPAH  QAPVAQTIIH  TVHSIPGQML  STPGIPPMAY  PTPAYTIPFF
Galectin5     ..........  ..........  .MSSFSTQT.  ..........  PYPNLAVPFF
Galectin4     FLGGQPAASQ  YPGTMTIPAY  PSAGYNPPQM  NSLPVMAGP.  PIFNPPVPYV
Galectin7     IF........  ..........  ..........  ..........  ..........
Galectin8     FRFSSDLQSM  ETSTLGLTQI  SKENIQKS..  ..........  GKLHLSLPFE
Galectin1     ..........  ..........  ..........  ..........  MACGLVASNL
Galectin2     ..........  ..........  ..........  ..........  MTGELEVKNM
Galectin3     GPIAPGAFPG  QPGGPGAYPS  APGAYPSAPG  AYPATGPFGA  PTGPLIVPYD 201                                                              250
      Uat     TSIPNGFYPS  KSINISGVVL  PDAKRFHINL  RCG..GDIAF  HLNPRFN...
Galectin5     TSIPNGLYPS  KSIVISGVVL  SDAKRFQINL  RCG..GDIAF  HLNPRFD...
Galectin4     GTLQGGLTAR  RTIIIKGYVL  PTAKNLIINF  KVGSTGDIAF  HMNPRIG...
Galectin7     ..........  ..........  ..........  ..........  ..........
Galectin8     ARLNASMGPG  RTVVVKGEVN  TNATSFNVDL  VAGRSRDIAL  HLNPRLN...
Galectin1     NLKPGECL..  ...KVRGELA  PDAKSFVLNL  GKD.SNNLCL  HFNPRFNAHG
Galectin2     DMKPGSTL..  ...KITGSIA  DGTDGFVINL  GQG.TDKLNL  HFNPRFS...
Galectin3     MPLPGGVMPR  MLITIIGTVK  PNANSITLNF  KKG..NDIAF  HFNPRFN.EN 251                                                              300
      Uat     .EKVVVRNTQ  INNSWGPEER  SLPGRMPFNR  GQSFSVWILC  EGHCFKVAVD
Galectin5     .ENAVVRNTQ  INNSWGPEER  SLPGSMPFSR  GQRFSVWILC  EGHCFKVAVD
Galectin4     .D.CVVRNSY  MNGSWGSEER  KIPYN.PFGA  GQFFDLSIRC  GTDRFKVFAN
Galectin7     ..........  ..........  ..........  ..........  ..........
Galectin8     .VKAFVRNSF  LQDAWGEEER  NITC.FPFSS  GMYFEMIIYC  DVREFKVAVN
Galectin1     DANTIVCNSK  DDGTWGTEQR  E..TAFPFQP  GSITEVCITF  DQADLTIKLP
Galectin2     .ESTIVCNSL  DGSNWGQEQR  E..DHLCFSP  GSEVKFTVTF  ESDKFKVKLP
Galectin3     NRRVIVCNTK  QDNNWGREER  Q..SAFPFES  GKPFKIQVLV  EADHFKVAVN
```

FIG. 2B

```
            301                                              336
      Uat   GQHICEYYHR  LKNLPDINTL  EVAGDIQLTH  VQT...
Galectin5   GQHICEYSHR  LMNLPDINTL  EVAGDIQLTH  VET...
Galectin4   GQHLFDFSHR  FQAFQRVDML  EIKGDITLSY  VQI...
Galectin7   ..........  ..........  ..........  ......
Galectin8   GVHSLEYKHR  FKDLSSIDTL  AVDGDIRLLD  VRSW..
Galectin1   DGHEFKFPNR  L.NMEAINYM  AADGDFKIKC  VAFE..
Galectin2   DGHELTFPNR  L.GHSHLSYL  SVRGGFNMSS  FKLKE.
Galectin3   DVHLLQYNHR  MKNLREISQL  GIIGDITLTS  ASHAMI
```

FIG.2C

NUCLEIC ACID ENCODING URATE TRANSPORTER AND METHODS OF USE THEREOF

CROSS-REFERENCE TO RELATED APPLICATION

This application is a continuation-in-part of U.S. patent application Ser. No. 09/221,898 filed Dec. 28, 1998 abandoned and provisional applications Serial No. 60/070,215, filed Dec. 31, 1997 and Serial No. 60/099,752 filed Sep. 10, 1998.

BACKGROUND OF THE INVENTION

The purine bases adenine and guanine, which are essential components of DNA, RNA and high energy phosphorylated compounds such as ATP and GTP, are either salvaged and re-utilized in the production of ribo- or deoxyribonucleotides or degraded by the enzyme xanthine oxidase to a relatively insoluble product, uric acid. As a first step in eliminating this intracellularly formed urate from the body, urate must exit cells. Thereafter, in most mammals, a large fraction of the extracellular urate enters peroxisomes of hepatocytes where it is oxidized by the enzyme uricase to a water soluble product, allantoin, which is then excreted by the kidneys. In other vertebrates, notably humans, some non-human primates, birds and reptiles, uricase is not expressed and, therefore, uric acid is the end product of purine metabolism. In all species, uric acid is ultimately cleared from the extracellular compartment via both the kidneys and intestine, with the former being the predominant excretory route.

Although all cells of the body that contain xanthine oxidase have the capacity to generate and accumulate urate intracellularly during the process of purine metabolism, there is no information on the mechanism(s) by which urate is transported out of cells into the extracellular compartment. Since the solubility of urate is quite low, an efficient mechanism must exist to prevent intracellular urate accumulation during periods of normal as well as accelerated nucleic acid turnover. Similarly, despite the important contribution of the intestine in the clearance of extracellular urate, with as much as one-third eliminated via this route in humans, there is minimal information on the mechanism(s) by which urate is transported by intestinal cells. In contrast, the participation of the kidney in disposing of urate has been extensively examined in multiple species. It is now generally accepted that urinary urate excretion occurs by a complex process that includes filtration at the glomerulus, and tubular reabsorption and secretion that take place primarily within the convoluted portion and pars recta of the proximal tubule. Two modalities of transport have been described in renal cortical cell membranes, an electroneutral anion exchanger that transports urate in exchange for a variety of organic and inorganic anions and an electrogenic urate transporter, a uniporter. Neither of these transporters have been identified and characterized at the molecular level.

The alteration of urate hemeostatis may result in elevated plasma levels of uirc acid, a condition known as hyperuricemia. Some hyperuricemia has a genetic basis, See, e.g. Scegmiller (1975) *Arthritis Rheum.* 18:743. Hyperuricemia may also result from the use of cytotoxic antineoplastic agents, or from diseases characterized by accelerated destruction of cells and increased turnover of nucleic acids, for example myeloproliferative disorders, leukemias, chronic hemolytic anemias, and multiple mycloma. Manifestations of hyperuricemia include gout and nephrotoxicity. Gout results from an inflammatory reaction to crystals of sodium urate deposited in joint tissue. Urate nephropathy results from precipitation of urate crystals in the renal tubules. Also, uric acid stones are common in the urinary tracts of patients with hyperuricemia. Urate transport may also be negatively affected by the use of nucleotide analogs in therapy of diseases such as HIV.

Accordingly, there is a need in the art for the characterization of urate transport mechanisms. The present invention provides nucleic acids encoding a urate transporter.

SUMMARY OF THE INVENTION

The present invention provides isolated nucleic acids encoding mammalian urate transporters (UATs). Such nucleic acids include those encoding the rat and human urate transporter. The present invention further provides vectors comprising the nucleic acids, host cells comprising the nucleic acid, and host cells comprising the vectors. Compositions comprising the vectors and a carrier are also provided.

In another embodiment, the present invention provides isolated and substantially purified urate transporters. Proteoliposomes containing substantially purified urate transporters are also provided, as well as compositions comprising the urate transporter and a carrier.

The present invention further provides methods of making a urate transporter, and methods of identifying agents that inhibit or agonize the transporter.

BRIEF DESCRIPTION OF THE DRAWINGS

FIG. 2 shows the alignment of UAT with the galectins. Shaded residues indicate identity between amino acids in UAT and the individual galectins. Alignment was produced using the University of Wisconsin Genetics Computer Group (GCG) program Best-Fit.

DETAILED DESCRIPTION OF THE INVENTION

Figure 1:
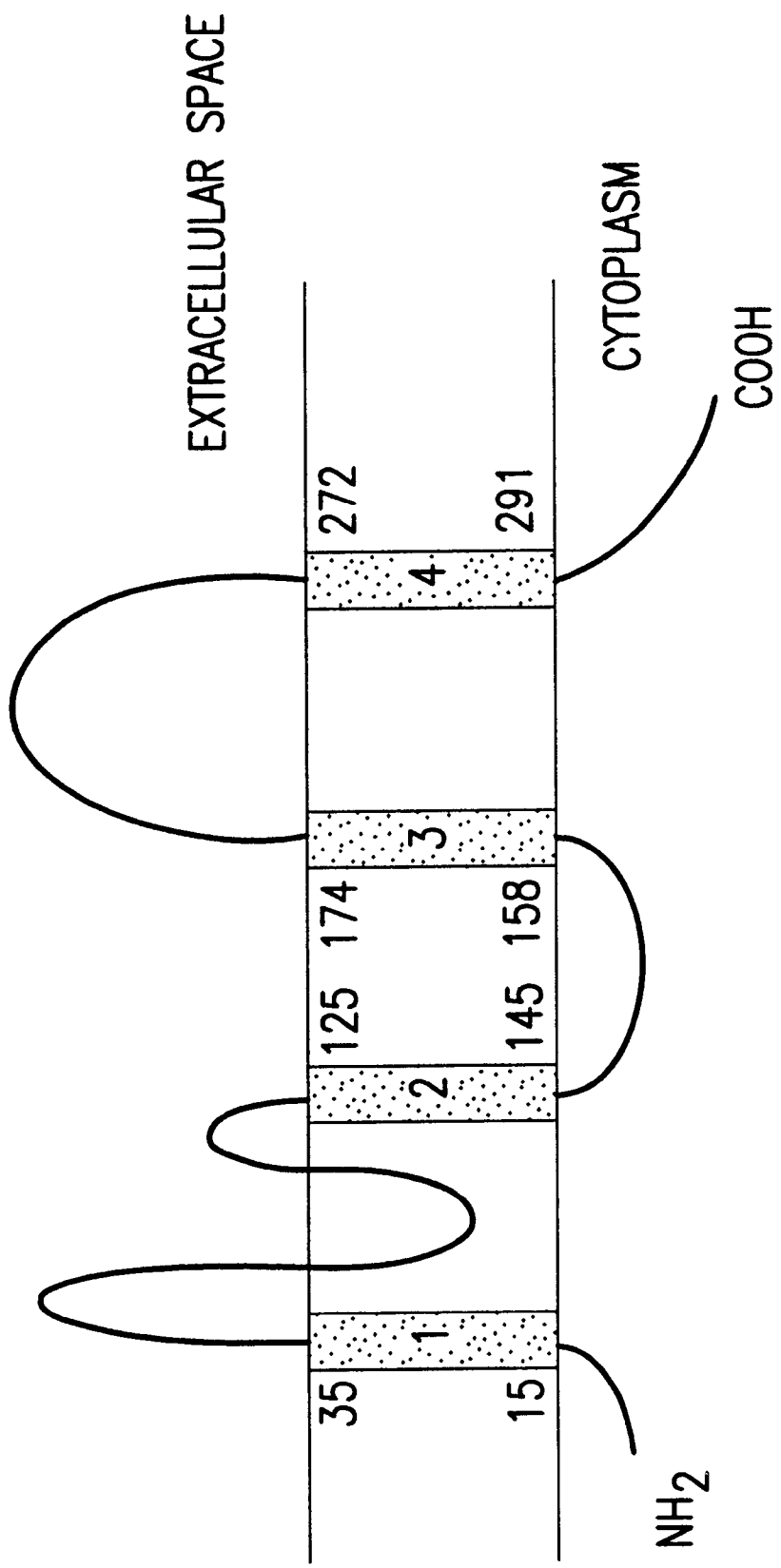
FIG. 1 is a structural model of UAT. Numbers 1–4 designate transmembrane domains. Numbers adjacent to transmembrane domains indicate the amino acid residues at the beginning and end of each transmembrane domain. The "loop" into the membrane designate the location of two β sheets that are connected by 6 amino acids that carry a net positive charge. The residues with homology to A1/A3 receptor, uricase, and the E and B loops of aquaporin-1 are 118–135, 151–185, 146–106 and 170–184, respectively.

The present invention provides isolated nucleic acids encoding urate transporters. A urate transporter is defined herein as a protein which, when functionally reconstituted in a planar lipid bilayer or expressed in a mammalian host cell, provides a highly selective urate channel. Those of ordinary skill in the art can use standard methods to assess channel activity and selectivity. For example, channel activity may be recorded using patch clamp methodology in the presence of symmetrical solutions of urate in buffers solutions of $K^+$, $Cs^-$, $Ca^{2+}$, $Cl^-$, and/or $SO^{2-}$. Clear transitions between open and closed states indicate single channel activity. Selectivity can be assessed using symmetrical solutions of urate with infinite gradients of $K^+$, $Cs^-$, $Ca^{2+}$, $Cl^-$, and/or $SO^{2-}$. Selectivity is indicated by lack of significant alteration of the current/voltage relationship in the presence of the infinite gradient. Further, the current/voltage relationship may be determined in the presence of a 10:1 urate gradient (cis to trans). A significant ($p<0.0001$) shift in equilibrium potential without a significant change in slope conductance resulting from the creation of the gradient confirms that the channel conducts urate and is highly selective.

In a preferred embodiment, the isolated nucleic acid has the sequence of SEQ ID NO: 1 or SEQ ID NO: 3. In another preferred embodiment the isolated nucleic acid has the sequence from nucleotide 84 to nucleotide 1052 of SEQ ID NO: 1 or the sequence from nucleotide 1 to nucleotide 969 of SEQ ID NO: 3, or a sequence having at least about 90% identity, and more preferably at least about 95% identity, to a nucleic acid having the sequence from nucleotides 84 to nucleotide 1052 of SEQ ID NO: 1 or from nucleotide 1 to nucleotide 969 of SEQ ID NO: 3. Percent identity for nucleic acids is measured using FASTA (Pearson et al. (1988) *Proc. Nat'l. Acad. Sci. USA* 85:2444. In another preferred embodiment, the isolated nucleic acid has a sequence that encodes the amino acid sequence of SEQ ID NO: 2 or SEQ ID NO: 4. In another preferred embodiment, the isolated nucleic acid has a sequence that encodes an amino acid sequence having at least about 90%. and more preferably at least about 95%, amino acid identity to the sequence of SEQ ID NO: 2 or SEQ ID NO: 4. Amino acid identity is calculated using the University of Wisconsin Genetic Computer Group (GCG) program Best-Fit. (Devereux et al. (1984) *Nucleic Acids Res.* 12:387).

SEQ ID NO: 1 is as follows:

```
   1 gtgaactcgt gggagtcccg ccctgtgcag agttctgtcc agcaagtgag gaagagagcg
  61 ttggttctcc cgaaacagaa gagatggctt tcttcagcac ccagcctcca tacatgaacc
 121 cagtcatccc ctttactgga ataatccaag gagggttgca gaacggactt cagatcaccc
 181 tccaggggac cgtccaccct tttccaaata ggattgcggt gaactttcag actggcttca
 241 gtggaaatga cattgccttc cacttcaatc cccggtttga ggaaggagga tatgtggttt
 301 gcaacacaaa gcagaatgga aagtgggggc ctgaggagag gaagatgcag atgcccttcc
 361 agaaggggat gccctttgag ctttgcttcc tggtacagag gtcggaattc aaggtgatgg
 421 tgaacaagaa cttctttgta cagtactcac accgcgtgcc ctaccacctc gtggacacca
 481 tttcggtctc gggatgcttg cacctgtcct tcatcaactt ccagactcag ggctttcagc
 541 ctgcccacca ggcacccgtg gctcaaacta tcatccacac agttcacagc atccctggac
 601 agatgctctc tactcctgga atccctccta tggcataccc cacccagcc tatactatac
 661 ctttcttcac cagcatccca aatgggtttt acccatccaa gtccatcaac atatcaggcg
 721 tggtcttgcc agatgctaag aggttccata tcaaccttcg ctgtgggggt gacattgctt
 781 tccacctgaa cccccgtttc aatgagaagg ttgtggtccg aaacactcag atcaacaact
 841 cctgggggcc cgaggagcga agcctgcctg ggagaatgcc cttcaatcgt ggccagagtt
 901 tctcagtgtg gatcttatgt gaaggtcact gcttcaaggt ggccgtggat ggtcagcata
 961 tttgtgaata ttaccaccgc ctgaagaact tgccggatat caacactcta gaggtggccg
1021 gtgatatcca gctgacacac gtgcagacct aggaaggtct ctggcttagg gatgaaggct
1081 gaggaaccct acctgagtct tgtcacctcc tccctgtctc agccctgcct ccccaaatcc
1141 tgtcatcaaa gagagcctca ttggcaggag ttccaggaag gtggcattcc caattcacac
1201 cctccacaaa gggggagtcc tgggctatgg gacacatggc tgtgagccca cagtgtcagc
1261 cattgctccc aagctagtca tcttctgagg gaagtgacct ccctgggttt gcccctttct
1321 ctgacctttc ccttcacccc tccaggaggg ccaccttgat gtcatcccat tggcctccag
1381 ctgacccaga atgtccacat taccttttcc ccaatctttc ccaatgccca taaaataaag
```

-continued

```
1441 aatatcaacg cttgtctaca aaaaaaaaaa aaaaaaaaaa aaaaaaaaaa
1501 aaaaaaaaaa aaaaaaaaaa aaaaaaaaaa aaaaaaaaaa aaaaa
```

SEQ ID NO: 2 is as follows:

MAFFSTQPPYMNPVIPFTGIIQGGLQNGLQITLQGTV

HPFPNRIAVNFQTGFSGNDIAFHFNPRFEEGGYVVCN

TKQNGKWGPEERKMQMPFQKGMPFELCFLVQRSEF

KVMVNKNFFVQYSHRVPYHLVDTISVSGCLHLSFIN

FQTQGFQPAHQAPVAQTIIHTVHSIPGQMLSTPGIPPM

AYPTPAYTIPFFTSIPNGFYPSKSINISGVVLPDAKRFH

INLRCGGDIAFHLNPRFNEKVVVRNTQINNSWGPEER

SLPGRMPFNRGQSFSVWILCEGHCFKVAVDGQHICE

YYHRLKNLPDINTLEVAGDIQLTHVQT

SEQ ID NO: 3 is as follows:

```
  1 atggccttca gcggttccca ggctccctac ctgagtccag ctgtcccctt ttctgggact
 61 attcaaggag gtctccagga cggacttcag atcactgtca atgggaccgt tctcagctcc
121 agtggaacca ggtttgctgt gaactttcag actggcttca gtggaaatga cattgccttc
181 cacttcaacc ctcggtttga agatggaggg tacgtggtgt gcaacacgag gcagaacgga
241 agctggggc cgaggagag gaagacacac atgcctttcc agaagggat gccctttgac
301 ctctgcttcc tggtgcagag ctcagatttc aaggtgatgg tgaacgggat cctcttcgtg
361 cagtacttcc accgcgtgcc cttccaccgt gtggacacca tctccgtcaa tggctctgtg
421 cagctgtcct acatcagctt ccagcctccc ggcgtgtggc ctgccaaccc ggctcccatt
481 acccagacag tcatccacac agtgcagagc gcccctggac agatgttctc tactcccgcc
541 atcccaccta tgatgtaccc ccaccccgcc tatccgatgc ctttcatcac caccattctg
601 ggagggctgt acccatccaa gtccatcctc ctgtcaggca ctgtcctgcc cagtgctcag
661 aggttccaca tcaacctgtg ctctgggaac cacatcgcct tccacctgaa ccccgttt
721 gatgagaatg ctgtggtccg caacacccag atcgacaact cctggggtc tgaggagcga
781 agtctgcccc gaaaaatgcc cttcgtccgt ggccagagct tctcagtgtg gatcttgtgt
841 gaagctcact gcctcaaggt ggccgtggat ggtcagcacc tgtttgaata ctaccatcgc
901 ctgaggaacc tgcccaccat caacagactg gaagtggggg gcgacatcca gctgacccat
961 gtgcagaca [tag]
```

SEQ ID NO: 4 is as follows:

MAFSGSQAPYLSPAVPFSGTIQGGLQDGLQITVNGTVLSSSGTRFAVNFQT

GFSGNDIAFHFNPRFEDGGYVVCNTRQNGSWGPEERKTHMPFQKGMPFDL

CFLVQSSDFKVMVNGILFVQYFHRVPFHRVDTISVNGSVQLSYISFQPPG

VWPANPAPITQTVIHTVQSAPGQMFSTPAIPPMMYPHPAYPMPFITTILG

GLYPSKSILLSGTVLPSAQRFHINLCSGNHIAFHLNPRFDENAVVRNTQI

DNSWGSEERSLPRKMPFVRGQSFSVWILCEAHCLKVAVDGQHLFEYYHRL

Nucleic acids encoding a urate transporter are isolatable from mammalian kidney. For example, such nucleic acids may be isolated by expression cloning by screening a mammalian kidney cDNA library using polyclonal or monoclonal antibodies specific for mammalian uricase, or polyclonal or monoclonal antibodies specific for mammalian urate transporter. In another example, isolated nucleic acids encoding a urate transporter may be isolated by using the nucleic acid having SEQ ID NO: 1 or SEQ ID NO: 3, or fragments thereof, as probes. The nucleic acid having SEQ ID NO: 1 or SEQ ID NO: 3, or fragments thereof, provide hybridization probes that can be used to isolate nucleic acids that hybridize thereto under high stringency conditions of 68° C. in aqueous buffered solution or at 42° C. in 50% formamide, and encode a urate transporter. Further, fragments of the nucleic acid of SEQ ID NO: 1 or SEQ ID NO: 3 provide PCR probes useful to isolate nucleic acids having at least 90%, or at least 95%, identity to a nucleic acid having the sequence of nucleotide 84 to nucleotide 1052 of SEQ ID NO: 1 or the sequence of nucleotide 1 to nucleotide 969 of SEQ ID NO: 3. The functional activity of the polypeptide encoded by the isolated nucleic acid can be determined by expressing the nucleic acid to provide a polypeptide, functionally reconstituting the polypeptide in a planar lipid bilayer by methods known in the art, and assessing channel activity and selectivity for urate as described hereinabove.

The present invention further provides a vector comprising an isolated nucleic acid encoding a urate transporter. In a preferred embodiment, the isolated nucleic acid had a sequence that encodes an amino acid sequence having at least about 90%, and more preferably at least about 95%, amino acid identity to the sequence of SEQ ID NO: 2 or SEQ ID NO: 4. In another preferred embodiment, the isolated nucleic acid is operably linked to an expression control sequence.

The present vectors are useful for the amplification and/or expression of nucleic acids encoding a urate transporter. Expression control sequences are transcriptional and/or translational regulatory elements that effect expression of the urate transporter in a suitable host cell. The expression control sequences may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful vectors can be constructed by methods known to one of ordinary skill in the art, and are also commercially available.

In a preferred embodiment, the vector is an expression vector comprising a strong constitutive or inducible promoter operably linked to a nucleic acid encoding a urate transporter. Suitable promoters are well known to those of ordinary skill in the art and include, for example, mammalian, bacterial, yeast, viral, and insect promoters.

In another embodiment, the present invention provides isolated and substantially purified urate transporter. In a preferred embodiment, the urate transporter has the amino acid sequence of SEQ ID NO: 2 or SEQ ID NO: 4, or an amino acid sequence that has 90% to 100% amino acid identity to the sequence of SEQ ID NO: 2 or SEQ ID NO: 4. In another preferred embodiment, the urate transporter is produced by expression of a nucleic acid encoding the urate transporter contained in a vector of the present invention.

In another embodiment, the present invention provides a proteoliposome containing substantially purified urate transporter. In a preferred embodiment, the urate transporter has the amino acid sequence of SEQ ID NO: 2 or SEQ ID NO: 4, or an amino acid sequence having about 90% to about 100% amino acid identity to the sequence of SEQ ID NO: 2 or SEQ ID NO: 4. Proteoliposomes may be prepared using methods well known to one of skill in the art, as disclosed for example by Leal-Pinto et al. (1995) *J. Membrane Biol.* 146:123, incorporated herein by reference.

The present invention further provides a host cell containing a nucleic acid encoding a urate transporter, and a host cell comprising a vector comprising a nucleic acid encoding a urate transporter. Host cells comprising the nucleic acids and vectors of the invention are useful for replicating and expressing the nucleic acid encoding the urate transporter. The host cell may be procaryotic or eukaryotic, including Xenopus oocyte, bacterial, yeast, insect and mammalian cells. Mammalian host cells are particularly preferred. Suitable mammalian host cells include, for example, commercially available cells such as LLC-PKI (pig kidney), MDCK (dog distal tubule), HEK-293 (human embryonic kidney) and rat inner medullary collecting duct cells.

The isolated nucleic acids and vectors of the invention may be introduced into host cells by methods known in the art, including transformation, transfection and infection. For example, transfection may be accomplished by known methods such as liposome mediated transfection, calcium phosphate mediated transfection, naked DNA transfection, microinjection and electroporation.

The present invention provides a method of making a urate transporter comprising introducing a nucleic acid encoding a urate transporter into a host cell, maintaining the host cell under conditions whereby the nucleic acid is expressed to produce the urate transporter, and recovering the urate transporter by methods known in the art.

The recombinant urate transporter produced by the nucleic acids and methods of the invention can be functionally reconstituted in a planar lipid bilayer. Methods for reconstituting transporter proteins in planar lipid bilayers are known to those of ordinary skill in the art, and disclosed for example by Leal-Pinto et al. (1995) *J. Membrane Biol.* 146:123; Leal-Pinto et al. (1997) *J. Biol. Chem.* 272:617–625; and Leal-Pinto et al. (1999) *J. Membrane Biol.* 169:13–27, incorporated herein by reference. For example, proteoliposomes containing the urate transporter are added to a lipid bilayer chamber and stirred until fusion occurs between the proteoliposomes and the lipid bilayer as evidenced by the presence of channel gating.

The present invention further provides a composition comprising a vector comprising a nucleic acid encoding a urate transporter, and a carrier. The invention also provides a composition comprising an isolated and substantially purified urate transporter and a carrier. The term "carrier" as used herein, includes any and all solvents, diluents, dispersion media, antibacterial and antifungal agents, microcapsules, liposomes, cationic lipid carriers, isotonic and absorption delaying agents, and the like.

In yet another embodiment, the present invention provides a method for identifying an agent that blocks a urate transporter, comprising contacting a urate transporter with an agent to be tested for its ability to block the urate transporter; measuring the channel activity of the urate transporter in the absence and presence of the agent; and comparing channel activity in the absence and presence of the agent, wherein a statistically significant reduction in channel activity in the presence of the agent is indicative of an agent that blocks the urate transporter. In a preferred embodiment, the urate transporter is functionally reconstituted and contained in a lipid bilayer. In another preferred embodiment, the urate transporter is recombinantly expressed in a mammalian host cell.

In another embodiment, the present invention provides a method for identifying an agent that agonizes a urate transporter, comprising contacting a urate transporter with a first agent to be tested for its ability to agonize the urate transporter, in the presence of a second agent that inhibits the urate transporter; and measuring the ability of the first agent to prevent the inhibition of channel activity by the second agent, wherein a statistically significant increase in channel activity in the presence of the first agent is indicative of an agent that agonizes the urate transporter. In a preferred embodiment, the urate transporter is functionally reconstituted and contained in a lipid bilayer. In another preferred embodiment, the urate transporter is recombinantly expressed in a mammalian host cell.

In a specific embodiment of the invention a number of activators of UAT channels were identified. For example, as described below copper was demonstrated to significantly increase UAT channel activity. Thus, administration of copper, copper chaperones, reagents that mimic the activity of copper, reagents that increase the delivery of copper to the UAT channel or reduce its removal from the UAT active site may be used to reduce the symptoms associated with hyperuricemia states.

When tested, lactose was also found to be a significant activator of UAT channel activity. Thus, the present invention further relates to administration of lactose, or other related carbohydrate molecules that increase the activity of UAT channel activity and which may be used to reduce the symptoms associated with hyperuricemic states.

In another embodiment of the invention, computer modeling and searching technologies will permit identification of potential activators of UAT channel activity. For example, based on knowledge of modifiers of channel activity and structural analysis and comparisons between urate transporters, the active sites of the UAT channel are identified. Such active sites might typically be located in the cytoplasmic or extracellular domains of the UAT channel. The active site can be identified using methods known in the art including, for example, from comparisons of the amino acid sequences of peptides, from the nucleotide sequences of nucleic acids, or from study of complexes between modifiers of UAT activity and the UAT channel.

The three dimensional geometric structure of the active site may be determined using known methods, including x-ray crystallography, which can determine a complete molecular structure. On the other hand, solid or liquid phase NMR can be used to determine certain intramolecular distances. Any other experimental method of structure determination can be used to obtain the partial or complete geometric structure of the UAT channel active site.

Having determined the structure of the active site, candidate modulating compounds can be identified by searching databases containing compounds along with information on their molecular structure. Such a search seeks compounds having structures that match the determined active site structure and that interact with the groups defining, the active site. Such a search can be manual, but is preferably computer assisted. These compounds found from this search are potential UAT modulating compounds.

Alternatively, these methods can be used to identify improved modulating compounds from an already known modulating compounds. The composition of the known compound can be modified and the structural effects of modification can be determined using experimental and computer modeling methods applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Although described above with reference to design and generation of compounds which could alter UAT activity, one could also screen libraries of known compounds, including natural products or synthetic chemicals, and biologically active materials, including proteins, for compounds which are modulators, i.e., inhibitors or activators, of UAT activity.

The nucleic acids, vectors, host cells, compositions, purified urate transporter, proteoliposomes, and methods of the present invention are useful for the characterization of the urate transporter. For example, these embodiments of the present invention are useful in identifying agents that modulate the channel activity of the urate transporter, and in determining the mechanism whereby certain chemotherapeutic and antiviral agents affect the activity of the transporter. For example, nucleoside analogs used in the treatment of HIV may interact with the xanthine binding site of the urate transporter of the present invention and thereby disrupt urate homeostasis. In accordance with the present invention, agents that prevent this interaction may be identified and used to ameliorate side effects of antiviral and anticancer chemotherapy. Further, the nucleic acids and related embodiments of the present invention are useful in the diagnosis of defects in the urate transporter The present invention provides for treatment or prevention of various diseases and disorders caused by hyperuricemia by administration of a compound that regulates the expression or activity of the UAT channel. Such diseases include those associated with hyperuricemia, including but not limited to myeloproliferative disorders, leukemias, chronic hemolytic anemias, multiple myeloma, gout, nephrotoxicity, uric acid stones, HIV, essential hypertension, cardiovascular disease, the metabolic syndrome of obesity, hypertriglyceridemia, glucose intolerance and hypertension (syndrome X), and a form of familial hyperuricemic nephropathy.

In a preferred embodiment, diseases and disorders involving hyperuricemia are treated or prevented by administration of a compound that activates UAT channel function. The compounds of the invention are preferably tested in vitro, and then in vivo for a desired therapeutic or prophylactic activity, prior to use in humans. For example, in vitro assays which can be used to determine whether administration of a specific therapeutic is indicated, include in vitro cell culture assays in which cells expressing the UAT channel are grown in culture, and exposed to or otherwise administered a therapeutic compound and the effect of such a therapeutic upon the transport of urate is observed. In a specific embodiment of the invention the ability of a compound to regulate, i.e., activate or inhibit urate transport may be assayed.

The invention provides methods of treatment and/or prophylaxis by administration to a subject of an effective amount of a compound of the invention. In a preferred aspect, the compound is substantially purified. The subject is preferably an animal, and is preferably a mammal, and most preferably human.

Various delivery systems are known and can be used to administer a compound capable of regulating UAT activity or expression, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The present invention also provides pharmaceutical compositions. Such compositions comprise a therapeutically effective amount of a compound capable of regulating UAT activity or expression and a pharmaceutically acceptable carrier. Such compounds include for example, copper, compounds that mimic the effect of copper, compounds that regulate the concentration of copper within a subject, lactose, and/or other carbohydrates that mimic the stimulatory activity of lactose on the UAT receptor.

In a specific embodiment, the term "pharmaceutically acceptable" means approved by a regulatory agency of the Federal or a state government or listed in the U.S. Pharmacopoeia or other Generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Oral formulation can include standard carriers such as pharmaceutical grades of mannitol, starch, magnesium stearate, sodium saccharine, cellulose, magnesium carbonate, etc. Examples of suitable pharmaceutical carriers are described in "Remington's Pharmaceutical sciences" by E. W. Martin. Such compositions will contain a therapeutically effective amount of the compound, preferably in purified form, together with a suitable amount of carrier so as to provide the form for proper administration to the patient. The formulation should suit the mode of administration.

The amount of the compound of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems.

The invention also provides a pharmaceutical pack or kit comprising one or more containers filled with one or more of the ingredients of the pharmaceutical compositions of the invention, optionally associated with such container(s) can be a notice in the form prescribed by a governmental agency regulating the manufacture, use or sale of pharmaceuticals or biological products, which notice reflects approval by the agency of manufacture, use or sale for human administration.

The following nonlimiting examples serve to further illustrate the present invention.

EXAMPLE 1

Materials and Methods

Expression Cloning

A rat whole kidney cDNA library (approximately $1.2 \times 10^6$ plaques) that was unidirectionally cloned in Uni-ZAP™ XR Vector using EcoR I and Xho I at the 5' and 3' ends, respectively (Stratagene, La Jolla, Calif.) was screened according to the Stratagene protocol with an affinity purified IgG fraction of a polyclonal antibody to pig liver uricase. This antibody was raised in rabbits to partially purified uricase (Sigma, St. Louis, Mo.) that was further enriched by affinity chromatography as described by Knorr et al. (1994) *J. Biol. Chem.* 269:6759. The IgG fraction of the antibody was obtained using a protein A antibody purification kit (Repligen, Cambridge, Mass.), concentrated to 10 mg/ml with Centricon 30 concentrators (Amicon, Beverly, Mass.), and then affinity purified on an ImmunoPure® Ag/Ab column (Pierce, Rockford, Ill.) to which pig liver uricase had been coupled. Western blots were performed using the picoBlue™ Immunoassay Kit (Stratagene) with a 1/5000 dilution of the antibody in Tris buffered saline containing 1% albumin. The library screen yielded one immunoreactive plaque which was designated UAT (urate transporter). The pBluescript phagemids in which UAT was inserted were excised in vivo from the Uni-ZAP vector and then rescued by transforming SOLR cells with the phagemids, as detailed by Stratagene. To determine insert size, colonies from plated SOLR cells containing pBluescript-UAT were grown in culture, maxi preps were performed (Qiagen Plasmid Maxi Kit, Qiagen Inc., Chatsworth, Calif.), plasmids were restriction digested with EcoR I and Xho I and then eleetrophoresed on 1% agarose gels.

Determination of Sequence of Full-length cDNA

Both strands of CAT were completely sequenced by automated sequence analysis using an Applied Biosystem Sequencer (ABI 373A) using dye terminator chemistry. To obtain the sequence of the full-length of the mRNA for UAT, rat renal poly $A^+$ RNA was subjected to reverse transcription (RT) and then rapid amplification of the 5' end of the cDNA by PCR using the 5'-AmpliFINDER™ RACE Kit (Clontech Laboratories, Inc., Palo Alto, Calif.). Poly A RNA was selected by affinity chromatography on oligo(dT)-cellulose as described by Chirgwin et al. (1979) *Biochem.* 18:5294 from RNA that was harvested from rat renal cortex as described by Sambrook et al. (1989) *Molecular Cloning: A Laboratory Manual*, $2^{nd}$ ed., pp. 7.1–7.87, Cold Spring Harbor Laboratory Press, N.Y. RT was performed using nucleotides 598–579 of the antisense strand of UAT as primer (SEQ ID NO: 1). After linking the AmpliFINDER anchor to the 3' end of the first-strand cDNA, PCR was performed using the AmpliFINDER anchor primer (complementary to the anchor) and two different nested primers. nucleotides 267–249 and 234–215 of the antisense strand of UAT. PCR was performed with Ampli Taq DNA Polymerase (Perkin Elmer, Roche) according to the Clontech protocol. PCR products were purified using the Wizard™ PCR Preps DNA Purification System (Promega, Madison, Wis.), subcloned into pCR™II vector using the TA Cloning® Kit (Invitrogen, San Diego, Calif.) and sequenced by automated sequence analysis as described above. Nucleotide sequences were analyzed using the Genetics Computer Group (GCG) Wisconsin sequence analysis package on a VAX mainframe computer to identify open reading frames. Database searches were preformed with the BLAST algorithms as described by Altschul et al. (1990) *J. Mol. Biol.* 215:403.

RT-PCR of UAT from Rat Kidney

Three separate preparations of poly $A^-$ RNA that were harvested from rat kidneys were reverse transcribed using random primers. Control reactions were performed in the absence of reverse transcriptase to assess the presence of contaminating DNA. PCR was carried out using nucleotides 249–267 of UAT as the sense primer and either nucleotides 1015–995 or 1272–1253 as the antisense primer (SEQ ID NO: 1). PCR was performed using an initial denaturation at 95° C. for 3 min, followed by 35 cycles of denaturation at 95° C. for 1 minute, annealing at 60° C. for 1 minute and extension at 72° C. for 2 minutes. After a final cycle that prolonged extension at 72° C. to 7 minutes, the samples were maintained at 4° C. To determine size, the PCR products were electrophoresed on 1% agarose gels. PCR products were purified, subcloned into pCR™ II vector, evaluated by restriction digestion with EcoR I, and sequenced using methods described above.

Northern Blot Analysis

Three cDNA probes were made for use in northern blots. Since UAT has an internal EcoR I site, one probe was made by restriction digestion of pBluescript-UAT with EcoR I. This 349 bp EcoR I fragment contains 5 bp of the 5' EcoR I site, 8 bp of the EcoR I linker (used in making the cDNA library), 14 bp of 5' non-coding sequence, and the initial 322 bp of the open reading frame of UAT (SEQ ID NO: 1). The second probe, prepared by restriction digestion of pBluescript-UAT with Sty I, provided a 902 bp probe encompassing nucleotides 147–1048 (SEQ ID NO: 1). The third probe, the linker probe, was made by PCR using pBluescript-UAT as template: nucleotides 456–476 (5' [GCGAATTCGTGCCCTACCACCTCGTGGAC] 3')(SEQ ID NO: 5) and nucleotides 638–618 of the antisense strand and (5'[GCGAATTCGTATGCCATAGGAGGGATTCC] 3') (SEQ ID NO: 6), constructed with EcoR I restriction sites at the 5' end of both primers, served as the sense and antisense primers, respectively (SEQ ID NO: 1). Conditions for PCR were identical to those described above. The PCR product was subcloned into the EcoR I site of pBluescript and both strands were sequenced as described above. Sequencing demonstrated that the PCR product was identical to the sequence in pBluescript-UAT. Each probe was radiolabeled with α-[$^{32}$P] dCPT (Dupont, NEN, Wilmington, Del.) using random primers (NEBlot™ Kit, New England Biolabs, Beverly, Mass.).

Two rat multiple tissue blots (Clontech) containing different preparations of poly A$^+$ RNA of each tissue were probed with the 3 different probes, described above, and a human β actin probe. Prehybridization, hybridization, rinsing and washing of the membrane at high stringency (0.1× SSC, 0.1% SDS at 65° C.) were performed according to the Clontech protocol. An additional multiple tissue blot (BIOS Laboratories, New Haven, Conn.) containing rat total RNA was examined with the linker probe, nucleotides 456–638 of UAT (SEQ ID NO: 1). This membrane was prehybridized, hybridized. rinsed and washed at high stringency (0.1×SSC, 0.1% SDS at 65° C.) according to the BIOS protocol. The nylon membranes were exposed at -70° C. to x-ray film (Kodak X-OMAT AR, Eastman Kodak, Rochester, N.Y.) using two intensifying screens for varying time periods.

Preparation of Recombinant Protein

The full-length of the coding sequence of pBluescript-UAT was amplified by PCR. The sense primer was constructed with a BamH I site immediately 5' to the start codon [5'GCGGATCCATGGCTTTCTTCAGCACCCAG 3'] (SEQ ID NO: 7) and encompassed nucleotides 84–104 of UAT. The antisense primer, constructed with a Pst I site [5'GCCTGCAGCTAGGTCTGCACGTGTGTCAGC 3'] (SEQ ID NO: 8) encompassed nucleotides 1052–1031 of UAT, including the stop codon (1050–1052)(SEQ ID NO: 1). PCR was performed under the following conditions: 95° C.×3 minutes, 35 cycles of 95° C.×30 seconds, 55° C.×45 seconds and 72° C.×2 minutes, followed by one additional cycle in which extension was prolonged to 7 minutes at 72° C., after which the sample was maintained at 4° C. The PCR product was purified and subcloned into pRSET A (Invitrogen Corp., San Diego, Calif.) to allow production of a fusion protein with a 6-histidine metal chelating domain 5' to the coding region of UAT. SURE cells (Stratagene) were transformed with pRSET A-UAT, plated colonies were grown in culture, a maxi prep was performed (Qiagen Plasmid Maxi Kit), and double restriction digests were done with combinations of EcoR I, BamH I and Pst I. Plasmids with inserts, as determined on agarose gel electrophoresis, were used to transform BL21(DE3)pLysE cells (Novagen, Inc., Madison, Wiss.).

Colonies of BL21(DE3)pLysE cells with pRSET A-UAT were grown overnight at 37° C. in 10 ml Super media (Qiagen) with Ampicillin (100 μg/ml). After centrifugation at 2500 rpm×10 minutes in a Sorvall RT6000 refrigerated centrifuge (DuPont Instruments) the cell pellet was resuspended in 10 ml fresh media, a 5 ml aliquot was added to a liter of identical media and then grown at 37° C. until the O.D. reached 0.7 when IPTG was added (0.4 mM final concentration). The culture was grown at 37° C. for an additional 2–4 hours, and then centrifuged at 5000×g for 20 minutes in a Sorvall RC-5B Refrigerated Centrifuge (Dupont Instruments) using a Model SLA-3000 Super Lite™ GS-3 rotor. Pelleted cells were stored at -70° C. until used. Following cell lysis, immobilized metal affinity chromatography was performed on a nickel chelating resin, Ni-NTA, (Qiagen Inc.) according to the Qiagen protocol for insoluble proteins. Eluate fractions containing peak protein concentrations (determined with the BioRad assay) were pooled, diluted to 0.1 mg/ml and dialyzed slowly at 4° C. to renature the recombinant protein: eluate to dialysis fluid volumes approximated 1:5. Dialysis solution urea concentration was progressively decreased from 8 to 0 mM as NaCl and glycerol were progressively added to 0.8 M and 10%, respectively: dialysis solutions were buffered to pH 7.5 with 0.02 M Tris HCl. SDS-PAGE with Coomassie Blue staining and western blots using 1/5000 dilution of the affinity purified IgG fraction of anti-pig liver uricase were performed pre and post dialysis.

Functional Assessment of Recombinant Protein

Preparation of Proteoliposomes

A mixture of bovine phosphatidyl-ethanolamine (PE, 10 mg/ml), and phosphatidylserine (PS, 10 mg/ml) (Avanti Polar Lipids, Birmingham. Ala.) in a ratio of 1:1 (wt/wt) was evaporated to dryness under nitrogen. The resultant phospholipid pellet was suspended in 48 μl of a solution containing 220 mM KCl, CsCl or $Cs_2SO_4$ and 10 mM HEPES-NaOH at pH 7.4. Following the addition of 2 μl recombinant UAT protein (50–100 μg/ml), proteoliposomes were formed by sonicating the mixture for 30 sec at 80 kHz in a bath sonicator (Laboratory Supplies, Hicksville, N.Y.) as described by Leal-Pinto et al. (1995) *J. Membrane Biol.* 146:123. In some experiments, proteoliposomes were prepared with the same lipids but with 10 μl recombinant HIV-1 Tat protein, as described by Zagury et al. (1996) *Cellular Pharm.—AIDS Sciences* 3:97 at 380 μg/ml and 40 μl of 220 mM $Cs_2SO_4$, 10 mM HEPES-NaOH at pH 7.4. Fresh proteoliposomes were prepared for each experiment.

Lipid Bilayer Chamber and Formation of Lipid Bilayer

The lipid bilayer chamber was identical to that described by Leal-Pinto et al. (1995) *J. Membrane Biol.* 146:123. The two cups of the plexiglass bilayer chamber were each initially filled with 1 ml of a solution whose electrolyte composition was identical to that in which the proteoliposomes were prepared. A 1:1 (wt/wt) mixture of bovine brain PE (10 mg/ml) and PS (10 mg/ml) (Avanti Polar Lipids) was dried with a nitrogen stream, dissolved in decane (Sigma Chemical Co.) to 50 mg lipid/ml and then painted with a club-shaped glass rod onto a 50 um hole in a Teflon film (Type C-20, 12.5 um thick, Dupont Electronics, Wilmington, Del.) that was fitted between the two cups of the chamber. Offset potentials due to all junction potentials were corrected by using the zero adjust system of the patch clamp amplifier (Model PC-501, Warner Instrument Co.). The voltage was subsequently clamped at varying levels (−100 to +100 mV): voltage was generated and controlled by the patch clamp amplifier. If a stable resistance of at least 100 gigohms and a noise of less than 0.2 pA were maintained, the experiments were initiated.

Channel Reconstitution

Experiments were initiated by adding proteoliposomes to the trans chamber (1 µl of UAT or 5–50 µl of HIV-1 Tat proteoliposomes). The solution was stirred until fusion occurred. Fusion usually occurred within 2–3 minutes of the addition of UAT-containing proteoliposomes, evidenced by the presence of channel gating (clear transitions between the closed and open states). Once fusion occurred the stirrers were stopped and the solution in the trans chamber was replaced with 1 ml of an identical solution, without proteoliposomes, to limit further channel incorporation. In all experiments channel activity was initially evaluated in the presence of symmetrical solutions of 2.5 mM urate in either 220 mM KCl, CsCl, or $Cs_2SO_4$, 10 mM HEPES-NaOH, and 0.25 mM $CaCl_2$ at pH 7.4. In some experiments channel activity was compared in the absence and presence of 5 mM $Ba^{+-}$. To evaluate channel selectivity, experiments were performed in symmetrical solutions of 2.5 mM urate, but with infinite gradients of $K^+$, $Cs^-$, $Ca^{--}$, $Cl^-$ and/or $SO_4^=$ established by using the following combination of buffered solutions in the cis and trans chambers, respectively: a) CsCl and KCl, b) $Cs_2SO_4$ and CsCl, and c) $Cs_2SO_4$ with $Ca^{-+}$ and $Cs_2SO_4$ without $Ca^{-+}$. Selectivity was also evaluated in symmetrical solutions of 220 mM $Cs_2SO_4$, 10 mM HEPES-NaOH, and 0.25 mM $CaCl_2$ at pH 7.4 in the presence of a 10:1 urate gradient: the 2.5 mM urate, buffered $Cs_2SO_4$ solution in the trans chamber was replaced with a $Cs_2SO_4$ solution containing 0.25 mM urate. In a final group of experiments, channel activity was compared in symmetrical solutions of 2.5 mM urate, 220 mM $Cs_2SO_4$, 10 mM HEPES-NaOH, and 0.25 mM $CaCl_2$ at pH 7.4 before and after an increasing amount of non-immune IgG (up to 200 µg) or the IgG fraction of antiporcine uricase (up to 15 µg) was sequentially added to each side of the lipid bilayer.

Data Collection and Analysis

Current output of the patch clamp was filtered at 1 kHz through an eight-pole filter (Bessel filter Model 902, Frequency Devices, Haverhill, Mass.) that was digitized at 2.5 kHz (Labmaster DMA Interface model TL-1, Axon Instruments, Burlingame, Calif.). Data were analyzed with commercial software (pCLAMP, Version 6.1, Axon Instruments) on a microcomputer after additional digitized filtering at not less than 100 Hz.

EXAMPLE 2

Nucleotide and Amino Acid Sequence of Cloned cDNA

A single plaque that expressed protein immunoreactive to anti-pig liver uricase was detected in a rat renal cDNA library. The cloned cDNA, which has been designated urate transporter (UAT), is 1476 bp. 5' extension of cDNA that was prepared by RT-PCR of rat renal cortical poly $A^{31}$ RNA extended the sequence 69 bp: there was no further extension of the cDNA when RT-PCR was repeated using a different, more 5' primer. The nucleotide sequence or the full-length cDNA is depicted in SEQ ID NO: 1 with the putative translation start site (ATG) at nucleotides 84–86, the stop codon (TAG) at 1050–1052, and the poly adenylation signal (AATAAA) at 1434: the poly A⁻tail consists of 86 bp. The presence of G at positions −3, −6 and +4 and the absence of T from −12 to −1, both relative to ATG at 84–86, as well as the fact that the ATG at this position is the first in the sequence support the assumption that the ATG at 84–86 is the actual initiation codon (Kozak (1987) *Nucleic Acids Res.* 15:8125). Utilizing this ATG as the start codon, the 1545 nucleotide sequence contains a 966 bp open reading frame that encodes a 322 amino acid protein with an estimated molecular weight of 36,341 daltons (GenBank accession number U67958).

Database searches with the deduced amino acid sequence of UAT indicated that this sequence is novel, with no linear sequence homology to uricase but with some degree of homology to a family of galactoside binding proteins, the galectins (galectin 1, accession number M19036, Clerch et al. (1988) *Biochem.* 27:692; galectin 2, accession number M87842, Gitt et al. (1992) *J. Biol. Chem.* 267:10601; galectin 3, accession number J02962, Albrandt et al. (1987) *Proc. Natl. Acad. Sci. USA* 84:6859, Barondes et al. (1994) *J. Biol. Chem.* 269:20807: galectin 4, accession number M73553, Oda et al. (1993) *J. Biol. Chem.* 26:5929; galectin 5, accession number L36862, Gitt et al. (1995) *J. Biol. Chem.* 270:5032; galectin 7, accession number L07769, Madsen et al. (1995) *J. Biol. Chem.* 270:5823; galectin 8, accession number U09824, Hadari et al. (1995) *J. Biol. Chem.* 270:3447). Alignment was produced using the GCG program Best-Fit, and is depicted in FIG. 2. UAT has the greatest degree of homology with galectin 5, a 145 amino acid protein of rat reticulocytes: 119 of 125 of the identical amino acids are localized in the carboxy terminus of UAT, between amino acid 186 and 322. Lesser homology is present between UAT and the other galectins. The percent amino acid identity between UAT and the galectins, as determined with the GCG program Best-Fit, are 24.2, 21.2, 34.0, 43.5, 85.2, 41.9, and 36.6 for galectin 1, 2, 3, 4, 5, 7, and 8, respectively. As is the ease with galectins 4 and 8, the sequence of UAT can be subdivided into 3 regions, a 124 amino acid $NH_2$ terminus, a 61 amino acid linker region, and a COOH terminus of 137 amino acids (FIG. 1). Although the amino and carboxy termini of UAT have homology with other galactoside binding proteins, and the termini have 41% identity with each other (GCG Best-Fit), the linker region is unique, revealing no significant homology to any protein listed in the databases.

The deduced amino acid sequence of UAT (SEQ ID NO: 2) has a number of possibly important sites and signatures (FIG. 1): two potential N-glycosylation sites (amino acids 209 and 251), 5 potential myristoylation sites within the amino terminus (amino acids 19, 23, 24, 28, 54), 3 potential phosphorylation sites including casein kinase II tyrosine kinase and protein kinase C (at amino acids 53, 64 and 122, respectively), and 2 vertebrate galactoside-binding lectin signatures (amino acid 81 and 254) (GCG program Motifs). Based on the method of Gamier et al that includes the assumption that at least 20% of the protein assumes a secondary structure, (Garnier et al. (1978) *J. Mol. Biol.* 120:97) UAT contains a stretch of 21 amino acids (97–117) that is predicted to assume the conformation of an alpha helix (FIG. 1). Alternative methods of analysis of the amino acid sequence do not predict an a helix that is long enough to span a membrane.

EXAMPLE 3

RT-PCR of UAT from Rat Kidney

To confirm the authenticity of the cDNA isolated by library screening, RT-PCR of poly A$^+$ RNA from rat kidney was performed with two sets of PCR primers that encompassed nucleotides 249–1015 and 249–1272 of the UAT cDNA. This resulted in the generation of PCR products that approximated those predicted on the basis of the number of nucleotides between the sense and antisense primers, 767 and 1024 nucleotides. Amplification products were not detected in the absence of reverse transcriptase, confirming the absence of contaminating DNA. Because EcoR I sites are present 5' and 3' to the PCR products that are subcloned into pCR™II, and UAT contains an internal EcoR I site, the sequences were evaluated by restriction digestion with EcoR I. Each PCR product yielded two fragments whose sizes were consistent with those predicted on the basis of an internal EcoR I site at nucleotide 405 of UAT (plus 10 bp of the vector 5' to the PCR product and 6 bp 3' of the product): 167 and 616 bp fragments for the smaller PCR product and 167 and 873 bp for the larger product. In view of the very high degree of homology between the carboxy terminus of UAT and galectin 5, the PCR products were also sequenced to assess the possibility that the cDNA that was cloned from the rat renal cDNA library might be chimeric. The nucleotide sequences of both PCR products were 100% identical to the sequence of UAT. Since both PCR products included the expected amino terminus, the linker region and the carboxy terminus of UAT, this finding indicates that the cDNA for UAT is not chimeric and that an mRNA for UAT is transcribed within renal tissue.

EXAMPLE 4

Northern Blot Analysis

Northern analysis of rat multi-tissue blots demonstrated that a cDNA probe representing the unique, linker region of UAT primarily recognizes a 1.55 kb mRNA in a variety of organs, including heart, brain, spleen, lung, liver, skeletal muscle, kidney and testes. mRNAs at approximately 6.0 and 7.5 kb are also recognized by this probe, but at much lower intensity. The detection of an mRNA that approximates 1.55 kb supports the conclusion that the 1545 bp sequence of UAT, which represents the sum of the nucleotide sequence of the clone from the cDNA library plus the 5' extension obtained by RT-PCR ofrat renal poly A$^-$ RNA, is the full-length sequence of UAT. It remains to be determined whether the larger mRNAs represent heteronuclear mRNA for UAT or alternate messages with significant homology to UAT. Although UAT mRNA has a wide tissue distribution, it is evident that there is differential expression of the mRNA with expression high in liver and very low in testes. Of interest, in a multi-tissue northern blot in which total (rather than poly A$^+$) RNA and the same probe were used, the 1.55 Kb mRNA was many fold more abundant in duodenum than in other tissue, including liver. Identical patterns were obtained with two other cDNA probes on two multi-tissue poly A$^+$ RNA blots; however, these alternate probes also recognized mRNAs that approximated 1.0 kb in heart and spleen. Since one probe (Sty I probe) covered both the amino and carboxy termini of UAT (nucleotides 147–1048), while the second (EcoR I probe) was confined to the amino terminus (through nucleotide 406), this smaller mRNA would appear to have a region of homology within the amino terminus of UAT. Thus, it is unlikely that the 1.0 kb mRNA in heart and spleen is galectin 5 since the high degree of homology between UAT and galectin 5 is located within the carboxy terminus of UAT.

EXAMPLE 5

Production of Recombinant UAT

SDS-PAGE analysis of induced bacterial lysates (BL21 (DE3)pLysE cells that had been transformed with pRSET A-UAT and stimulated with IPTG to produce recombinant UAT protein) revealed a 36–37 kd band that was absent in BL21(DE3)pLysE cells that were transformed with the same vector (pRSET A) without UAT. Western blots demonstrated that the 36–37 kd protein was reactive to the affinity purified IgG fraction of rabbit anti-pig liver uricase. Following affinity chromatography on a Ni-NTA resin the purified protein, which was eluted in 8M urea at pH 4.5, was extensively dialyzed to both renature the protein and change the solute content and pH. SDS-PAGE with Coomassie Blue staining indicated that the dialyzed, affinity purified protein was identical in size to that identified in lysates of cells transformed with pRSET A-UAT and western blots demonstrated that the protein remained immunoreactive to anti-pig liver uricase.

EXAMPLE 6

Functional Assessment of Recombinant Protein

Single channel activity (evidenced by clear transitions between the open and closed states) was detected in symmetrical urate solutions following fusion of recombinant UAT containing proteoliposomes with the lipid bilayer. Both the closed and open time histograms fit single exponential curves suggesting that only one type of channel was present and that this channel has single open and closed states. In contrast to the channel activity that was evident within minutes of addition of UAT containing proteoliposomes to the chamber, no channel activity was detectable when proteoliposomes containing an unrelated protein (recombinant HIV-1 Tat protein) was utilized. Since recombinant UAT and HIV-1 Tat proteins were both generated in BL21(DE3) pLysE cells, and both proteins were purified and renatured by the same methodology, it was concluded that the channel is specific to UAT and not a channel that derives from a bacterial protein that might have co-purified with UAT.

The mean current/voltage relationship was determined in 11 experiments performed in symmetrical urate solutions. Linear regression analysis of the mean currents at positive and negative voltages yielded a slope conductance of 9.5±0.47 pS®=0.99). The reversal potential was not significantly different from zero (3.0±2.8 mV). To assess the channel's selectivity, the current/voltage relationship was assessed in symmetrical solutions of 2.5 mM urate and 220 mM KCl, with and without 5 mM Ba$^{++}$. Ba$^{+-}$ failed to alter channel activity, indicating that the reconstituted channels are not K$^-$ channels. This conclusion was supported by the finding that the current/voltage relationship was not altered when urate was dissolved in symmetrical solutions of 220 mM CsCl or Cs$_2$SO$_4$ rather than KCl or when an infinite gradient for K$^+$ was created. The current/voltage relationship that was observed with symmetrical urate and salt solutions was also not significantly changed in the presence of infinite gradients of Cs$^+$, Ca$^{++}$, Cl$^-$ or SO$_4^{--}$. Since these observations indicate that the channel is minimally permeant to K$^+$, Cs$^+$, Ca$^{-+}$, Cl$^-$ and SO$_4^{--}$, it seemed likely that the current was carried by urate. To more directly assess the ability of the channel to conduct urate, the current/voltage relationship was determined in the presence of a 10:1 urate gradient (cis to trans). Creation of a urate gradient resulted in a significant shift (p<0.0001) in the equilibrium potential to 38.3±3.3 mV, a value that approaches the equilibrium potential for urate. This change in equilibrium potential occurred without a significant change in slope conductance (10.8±0.63 pS versus 9.5±0.47 pS in the presence and absence of the urate gradient). This finding confirms that the channel conducts urate and indicates that it is highly selective for this organic anion. Finally, the polyclonal antibody that was used to select UAT from the cDNA library (the IgG fraction of anti-pig liver uricase) significantly decreased the open probability of the channel and increased the probability that the channel would be in the closed or inactive state. This effect was dose dependent, with channel activity abolished after addition of 10 μg of antibody. In contrast, the IgG fraction of non-immune serum flailed to alter channel activity.

The foregoing examples demonstrate the cloning of a novel full-length cDNA, UAT, that encodes a 322 amino acid protein by screening a rat renal cDNA library with a polyclonal antibody to pig liver uricase. UAT mRNA for this sequence was present, but differentially expressed in multiple tissues. Recombinant protein that was produced from the cloned cDNA approximated the size (36–37 kd) that was estimated from the deduced amino acid sequence. The cDNA sequence revealed no homology to uricase, but the recombinant protein was immunoreactive to anti-pig, liver uricase. Further, functional assessment indicated that a voltage sensitive ion channel was reconstituted when this recombinant protein was fused with planar lipid bilayers. In contrast, no channel activity was detected in the presence of an alternate recombinant protein, HIV-1 Tat. Of note, the ion channel that was encoded by the cloned cDNA was highly selective to the organic anion urate relative to the inorganic ions potassium, cesium, calcium, chloride and sulfate, and activity of this channel was blocked by the same antibody that identified the cDNA clone in the rat renal library.

The foregoing examples further demonstrate that the deduced amino acid sequence of UAT exhibits homology with the galectins, a family of β-galactoside binding proteins previously referred to as S-Lac lectins (soluble lactose-binding vertebrate lectins). Seven members of the galectin family have been identified to date, galectins 1–5, 7 and 8. The tissue distribution of each type of galectin differs considerably. However, within tissues they have generally been localized to the cell cytoplasm although some, despite the absence of a classical signal sequence, are also externalized to the extracellular compartment. It is of note that none have been reported to be localized to cell membranes. Since the antibody that was used to clone and characterize UAT recognizes an identical protein in renal tissue, then the results of Knorr et al. (1994) *J. Biol. Chem.* 269:6759 imply that UAT, unlike the galectins, resides within renal cell membranes: urate binding proteins that were affinity purified from renal cell membranes were immunoreactive to this antibody, urate transport across renal membrane vesicles was specifically inhibited by anti-pig liver uricase, and immunoreactivity to this antibody was localized to brush-border membranes of renal proximal tubules. In addition to UAT having a novel cellular localization relative to members of the galectin family, none of the previously described galectins have been considered to function as membrane transporter/channels. In fact, the biologic function(s) of the reported galectins remains to be established. Rather, galectins have been postulated to play a role in cell migration and adhesion, in the regulation of cell proliferation, in immune function and in neoplasia.

EXAMPLE 7

Localization of UAT in the Human Kidney

Since the polyclonal antibody that detected the full-length clone encoding UAT selectively inhibits electrogenic urate transport in intact rat renal membrane vesicles and, by immunolocalization, detects UAT in rat PT, this antibody was used to determine if the urate transporter/channel is also expressed in human kidney. Human fetal kidney (HFK) at ages 12–24 weeks, newborn (NB) and adult (NHK) kidneys were immunolabeled with anti-UAT. At all ages of HFKs, UAT was only detected in the cytoplasm of well-developed PTs (those with brush-borders detectable by Periodic Acid Schiff staining): UAT was not detected in either the nephrogenic zone or in mature glomeruli or other tubular segments in the renal cortex. In NB kidneys, labeling was also confined to the cytoplasm of PT cells. In contrast, in 2–41 year old NHK, labeling was localized to brush-borders of S1 PT segments. This late, postnatal expression of UAT in apical membranes contrasts with the early prenatal expression of other apical transporters (e.g. aquaporin-2). Of interest, premature and newborn human kidneys excrete a very high fraction of filtered urate; thereafter, when the concentrating capacity of the kidney increases, fractional excretion decreases attaining low, adult levels by 1–2 years. The present observations indicate that the developmental change in localization of UAT from cytoplasm to brush-border membranes may be responsible for the important postnatal change in renal urate transport.

EXAMPLE 8

Inhibitors of Renal Electrogenic Urate Transport Block Recombinant Urate Transporter/Channel Activity To characterize the relationship between UAT and the renal electrogenic urate transporter, the effects of known inhibitors of the electrogenic transporter, oxonate and pyrazinoate (PZA), on UAT channel activity were examined. Recombinant UAT was incorporated in liposomes and subsequently fused with a lipid bilayer made with the same lipids. In symmetric 2.5 mM urate solutions a voltage dependent 10 pS urate channel was detected. In the presence of bi-ionic conditions (2.5 mM urate cis: 2.5 mM oxonate trans) neither channel activity nor voltage sensitivity of the channel were initially influenced by the presence of 2.5 mM oxonate in the trans chamber. However, in contrast to studies performed in symmetrical urate solutions (without oxonate) in which channel activity is detectable for many hours, in each experiment performed under these bi-ionic conditions channel activity ceased after approximately one hour. The mechanism for this delayed blockade of channel activity was assessed by adding aliquots of the 2.5 mM oxonate solution to either the cis or trans chamber after channel activity was recorded in symmetrical urate solutions. As anticipated from the activity of the channel in the presence of 2.5 mM oxonate in the trans chamber, channel activity was not affected by 250 μM oxonate on the trans side of the channel. In contrast, open probability of the channel progressively decreased as the concentration of oxonate was sequentially increased on the cis side of the channel. Channel activity was 97% blocked at an oxonate concentration of 108±16 μM (mean±SE, n=3) in the cis chamber. The oxonate induced block was reversed by replacing the oxonate containing solution in the cis chamber with oxonate-free solution. The asymmetrical effect of oxonate oil channel activity indicates that the delayed block that was observed under bi-ionic conditions resulted from accumulation of oxonate in the cis chamber subsequent to its trans to cis flux through the channel. Based on the channel's orientation in the bilayer, this unilaterally induced block in channel activity indicates that oxonate interacts with a specific domain in UAT that is located on the cytoplasmic (cis) face of the channel whereas the extracellular domain(s) of UAT lack an oxonate binding site.

PZA, like oxonate, induced a dose dependent block of urate channel activity that was reversed by replacing the PZA-containing solution in the chamber with fresh PZA-free urate solution. However, in distinct contrast to oxonate, PZA only induced a block in urate channel activity when present in the trans chamber: PZA was without effect when added to the cis chamber. PZA completely blocked channel activity at a concentration of 24.1±8.9 $\mu$M (mean±SE, n=8) in the trans chamber. Based on the orientation of the urate channel in the lipid bilayer, the consistent unilateral trans effect of PZA implies that this agent interacts with a specific domain in UAT that is confined to the extracellular (trans) face of the channel. Since oxonate and PZA block channel activity of recombinant UAT and inhibit renal electrogenic urate transport, this example, in conjunction with the foregoing examples, indicates that UAT is the molecular representation of the electrogenic urate transporter.

EXAMPLE 9

Molecular Modeling of UAT

The amino acid sequence of UAT was assessed with the multiple protein sequence alignment program MACAW (Schuler et al. (1991) *Proteins; Struct; Funct; and Genetics* 9:180). Amino acid residues 151–185 of UAT showed 49% homology to residues 230–264 of porcine uricase (Wu et al. (1989) *Proc. Nat'l. Acad. Sci.* 86:9412) and 31% homology to residues 223–257 of Aspergillus uricase (Legoux et al. (1992) *J. Biol. Chem.* 267:8565).

Because xanthine and urate were equally effective as ligands to affinity purify urate binding proteins from rat renal plasma membranes, and xanthine is a competitive inhibitor of uricase, the effect of xanthine on urate channel activity was also evaluated. In contrast to the unilateral effects of anti-uricase and oxonate, xanthine blocked channel activity when present on either the extracellular or cytoplasmic side of UAT. The concentration of xanthine (4.6±1.5 $\mu$M, mean±SE, n=5) that was required to completely block channel activity when added to the extracellular side of UAT was approximately one-tenth that which blocked from the channel's cytoplasmic face. These results are consistent with an interaction of xanthine with amino acids within a block of homology to uricase on the cytoplasmic side of UAT and also indicate that an additional binding site with high affinity for xanthine is present within the extracellular domain of UAT.

Based on the observation that xanthine blocks channel activity from both the cytoplasmic and extracellular sides of UAT, local blocks of homology were also sought between UAT and proteins, other than uricase, with known xanthine binding sites. Amino acid residues 118–135 of UAT showed 61% homology to amino acids 241–258 of the rat A1 adenosine receptor (Mahan et al. (1991) *Mol. Pharmacol.* 40:1) and 50% homology to residues 239–256 of the rat A3 adenosine receptor (Zhou et al. (1992) *Proc. Nat'l. Acad. Sci.* 89:7432). It is in this region of the A1 and A3 receptors, specifically residues P249, H351 and N254 of the A1 receptor that xanthine (and adenosine) bind. These amino acids of the A1 receptor align with P126, H128 and D131 of UAT. Adenosine, like xanthine is a potent blocker of UAT channel activity when added to the extracellular side of the channel: a total block of channel activity was observed at an adeonsine concentration of 4.6±2.6 $\mu$M (mean±SE, n=3). However, in contrast to xanthine, adenosine failed to block channel activity when applied to the cytoplasmic domain of UAT (n=3). Based on the unilateral effect of adeonsine on channel activity, the adenosine-like binding site in UAT may be localized, at least in part, to the extracellular domain of the protein. Since xanthine has a high affinity for the A1/A3 receptor, it is presumed that the block in channel activity that is induced by xanthine in the trans chamber is consequent to binding to amino acid residues within this extracellular domain of UAT.

The above results provide strong evidence that residues 118–135 of UAT (the region with homology to the adenosine receptor) must be separated from residues 151–185 (the region with homology to uricase) by a transmembrane domain. The program TopPred II (Claros et al. (1994) *Comput. Appl. Biosci.* 10:685) was used to determine if a hydrophobic domain is likely to span the membrane between these regions. The corresponding hydrophobicity profile of UAT, as calculated using the Kyte-Doolittle scale (Kyle et al. (1982) *J. Mol. Biol.* 157:105), clearly indicates the existence of a hydrophobic peak located between residues 128–148. Within this portion of UAT, amino acids 125–145 of UAT are predicted to form an $\alpha$-helix: this membrane spanning domain would connect the extracellular region of UAT that has homology to the A1/A3 receptor to the intracellular region that has homology to uncase. This predicted $\alpha$-helix has 38% homology (3 identical, 5 conserved amino acids) to the $\alpha$-helix that has been documented by x-ray crystallography to form transmembrane domain E (residues 134–156) in bacterial rhodopsin (Pebay-Peyroula et al. (1997) *Science* 277:1676). This same region of UAT also has 30% homology (3 identical, 4 conserved amino acids) to the $\alpha$-helix that is predicted to form transmembrane domain 3 (residues 162–184) of uric acid/xanthine permease, a fungal urate/xanthine transporter (Garfinkel et al. (1993) *J. Biol. Chem.* 268:23376) that is otherwise unrelated to UAT.

Utilizing TopPred II, three additional $\alpha$-helices are predicted in UAT: residues 15–35, 158–174 and 272–291: the hydrophobicity profile indicates that these are hydrophobic segments long enough to span the membrane. The putative transmembrane domain composed of amino acids 158–174 of UAT has 59% homology (3 identical, 7 conserved amino acids) to a portion of the $\alpha$-helix that has been reported by x-ray crystallography to form transmembrane domain IX (residues 336–357) of subunit 1 of cytochrome C oxidase (Tsukihara et al. (1996) *Science* 272:1136).

In addition to the above noted four putative transmembrane $\alpha$-helices, two $\beta$ sheets are predicted in UAT encompassing amino acids 96–104 and 111–119 of UAT. These residues are long enough to traverse the membrane and, because both $\beta$ sheets are amphiphilic, may represent a pore-like domain that can move in and out of the membrane. This region of the protein, along with the intervening amino acids (105–110) which carry a net positive charge (R, K, and E), may function as the voltage sensor in UAT.

The foregoing observations provide a rationale for a molecular model of UAT in which UAT has four membrane spanning domains and both its amino and carboxy termini are located intracellularly (FIG. 1). In this model the four transmembrane $\alpha$-helices in the single EAT molecule encircle and thereby form a central stable hydrophilic pore-like structure within the membrane.

EXAMPLE 10

Cellular Localization of a Cloned Urate Transporter/Channel

As demonstrated in the foregoing examples, the 36 kd recombinant protein (UAT) that was prepared from a cloned rat renal cDNA has been shown to be a urate transporter/channel when fused with lipid bilayers. To elucidate the cellular localization of UAT, cDNAs were constructed with green fluorescent protein (GFP) linked to the amino or carboxy terminus of UAT and subcloned into pGEMHE. cRNAs (up to 10 ng), transcribed from the cDNAs with an in vitro transcription kit, were injected into stage 5–6 *Xenopus laevis* oocytes. Oocytes were fixed, sectioned, and examined by confocal microscopy 48 hours after injection. Injection of both the amino and carboxy terminal constructs resulted in weak expression with fluorescence that appeared to be restricted to the Golgi apparatus. To determine if a similar pattern of localization was present in mammalian cells, a cDNA was constructed with GFP linked to the carboxy terminal of UAT and subcloned into pcDNA3.1(–). HEK 293 cells were transiently transfected with the UAT-GFP construct or GFP using the TransFast lipofection reagent. Plasma membranes were stained with the fluorescent probe Hoechst. Confocal microscopy performed 24 hours post transfection revealed that (UAT-GFP was heavily expressed and colocalized with PKH26 in plasma membranes. UAT-GFP was also detected in Golgi. GFP, without UAT, was located diffusely in the cytoplasm and nuclei. These results indicate differential localization of UAT in 293 cells and Xenopus oocytes that may represent differences in targeting and/or degradation. In addition, since UAT is targeted to plasma membranes in a mammalian cell line, these findings indicate that UAT functions to transport urate electrogenically across renal proximal tubule plasma membranes as well as across artificial lipid bilayers.

EXAMPLE 11

Galactin 9 is the Human Urate Transporter/Channel Homologue

Galactin 9 was reported to be a secreted neutrophil chemoattractant. However, galectin 9 has more than 75% amino acid homology to the rat urate transporter/channel. To test whether galectin 9 is the human plasma membrane-associated urate transporter channel, cDNA was generated by RT-PCR of RNA from WBC of a normal donor and fused with an amino terminal 6-histidine tag in a bacterial expression vector. Recombinant protein (hUAT) was prepared and then purified on a Ni-NTA column. hUTA was sonicated into liposomes, fused with a lipid bilayed, and channel activity was recorded. Channel activity was only detected in the presence of urate. The channel exhibited a conductance of 5pS, approximately half that of the rat UAT. As in the rat, the human urate transporter/channel was highly selective for urate as compared to Cs+, Ca+–, SO4––, or Cl-. As predicted by the high degree of homology between the adenosine-binding site in hUAT and that in rat UAT, adenosine blocked channel activity from the trans side of the bilayer. Similar to rat, the specific inhibitor pyrazinamide blocked channel activity from the same (trans) side of the bilayer as adenosine, indicating that the membrane topography of the two channels is homologous. However, unlike rat UAT, hUAT showed minimal voltage sensitivity. This difference in voltage sensitivity is consistent with the absence of a positively charged amino acid in hUAT in a region of the putative voltage sensing loop within rat UAT.

To assess its cellular localization and topology, hUAT cDNA was fused to either GFP or a FLAG epitope at its amino- or carboxy-termini in a mammalian expression vector, and transfected into LLC-PK1 cells. FLAG epitope was detected by immunocytochemistry, and GFP by direct fluorescence. Cellular localization was determined by confocal microscopy. Using Clontech human multi-tissue RNA blot, the tissue distribution of hUAT mRNA was assessed with a 180 bp probe that is unique to hUTA. hUTA protein fused with the lipid bilayer resulted in channel acivity which, like rat UTA, was highly selective for urate. Transfection of hUTA constructs fused with FLAG or GFP on either amino or carboxy termini always resulted in hUTA expression in plasma membranes of LLC-PK1 cells. Further, plasma membrane-associated FLAG epitope was only detected in permeabilized cells, indicating that both amino and carboxy termini of hUAT are cytosolic. As in the rat, the mRNA for hUAT is differentially expressed in multiple tissues.

EXAMPLE 12

Identification Of Urate Transporter Activators

In a continued search for local blocks of homology between rat and human UAT and known proteins, a highly significant block of homology to copper chaperones was detected in the carboxy terminus of both the rat and human UAT. Based on the possibility that this portion of UAT binds copper, like copper chaperones, experiments were conducted to determine whether copper was able to modulate UAT channel activity. Using rat and human recombinant UAT it was observed that copper plays an important role in modulating channel activity. Increasing ambient copper by addition of less than 1 $\mu$M copper to the bathing solution significantly increases channel activity (increasing open probability of the human channel from 5–15% to greater than 50–60%), whereas the addition of less than 1 $\mu$m of a specific copper chelator to an activated channel significantly reduces channel activity (to being inactive close to 100% of the time).

It is of note that Wilson's disease, an inherited disease with excessive copper deposition in multiple tissues, including the kidney, is associated with low plasma urate concentrations in combination with increased rates of renal urate excretion. The low plasma urate concentration is a rather consistent finding and has been used as diagnostic tool to suggest Wilson's disease as the etiology of cirrhosis in relatively young individuals. Based on the observation that copper increases the activity of UAT, it is likely that the increased rates of urate excretion (and consequent reduction in plasma urate concentration) in Wilson's disease is secondary to activation of UAT channel activity and the consequent increased urate secretion due to increased free copper concentrations in renal epithelial cells. Thus, reagents that mimic the effect of copper, increase the delivery of copper to the channel, or reduce its removal from the active site would be useful agents in the management of hyperuricemic states (such as seen in essential hypertension, cardiovascular disease, the metabolic syndrome of obesity, hypertriglyceridemia, glucose intolerance and hypertension, syndrome X, a form of familial hyperuricemic nephropathy that results in renal failure and primary gout).

The rat and human urate transporter/channel amino acid sequence contains two galactose binding sites. In the molecular model of the urate transporter/channel, both of these sites reside in extracellular domains of the protein. One site is located between the putative first and second transmembrane domain, the second is located between the putative third and fourth transmembrane domains. Experiments indicate that the addition of lactose (less than 50 µM) to the side of the bilayer chamber that is believed to face the extracellular domains of the protein alters the biophysical properties of the human urate transporter channel. Subsequent to addition of lactose there is an increase in current and an apparent stabilization of the channel in the lipid bilayer. It is believed that the increase in current is consequent to oligomerization of monomers of the protein in the bilayer. Insofar as current is increased in the presence of lactose, and ion flow is increased, then this reagent (and perhaps other comparable compounds) can also be considered to stimulate urate flux across the channel. In vivo, this could result in increased urate excretion and ultimately a reduction in plasma urate concentration.

All of the references cited herein are incorporated by reference in their entirety.

We claim:

1. An isolated nucleic acid encoding a urate transporter comprising the nucleotide sequence of SEQ ID NO:3.

2. An isolated nucleic acid comprising the nucleotide sequence from nucleotide 1 to nucleotide 969 of SEQ ID NO:3.

3. An isolated nucleic acid comprising a nucleotide sequence that encodes the amino acid sequence of SEQ ID NO: 4.

4. A vector comprising the nucleic acid of claim 1, 2 or 3.

5. The vector of claim 4 wherein said nucleic acid is operably linked to a promoter.

6. A host cell comprising the isolated nucleic acid of claim 1, 2 or 3.

7. A host cell comprising the vector of claim 4.

8. The host cell of claim 6 or 7 wherein said host cell is a Xenopus oocyte, bacterial, yeast or insect cell.

9. The host cell of claim 6 or 7 wherein said host cell is a mammalian cell.

10. A method of making a urate transporter comprising introducing the nucleic acid molecule of claim 1, 2 or 3 into a host cell, and maintaining the host cell under conditions whereby the nucleic acid is expressed to produce the urate transporter.

11. The method of claim 10 further comprising the step of recovering the urate transporter.

12. The method of claim 10 wherein said host cell is a bacterial, yeast or insect cell.

13. The method of claim 10 wherein said host cell is a mammalian cell.

14. A composition comprising the vector of claim 4 and a carrier.

* * * * *

SEQUENCE LISTING

<160> NUMBER OF SEQ ID NOS: 8

<210> SEQ ID NO 1
<211> LENGTH: 1545
<212> TYPE: DNA
<213> ORGANISM: Rat

<400> SEQUENCE: 1

```
gtgaactcgt gggagtcccg ccctgtgcag agttctgtcc agcaagtgag gaagagagcg      60
ttggttctcc cgaaacagaa gagatggctt tcttcagcac ccagcctcca tacatgaacc     120
cagtcatccc ctttactgga ataatccaag gagggttgca gaacggactt cagatcaccc     180
tccaggggac cgtccaccct tttccaaata ggattgcggt gaactttcag actggcttca     240
gtggaaatga cattgccttc cacttcaatc cccggtttga ggaaggagga tatgtggttt     300
gcaacacaaa gcagaatgga aagtgggggc ctgaggagag gaagatgcag atgcccttcc     360 agaagggat gcccttgag ctttgcttcc tggtacagag gtcggaattc aaggtgatgg     420
tgaacaagaa cttctttgta cagtactcac accgcgtgcc ctaccactc gtggacacca     480 tttcggtctc gggatgcttg cacctgtcct tcatcaactt ccagactcag ggctttcagc     540
ctgcccacca ggcacccgtg gctcaaacta tcatccacac agttcacagc atccctggac     600
agatgctctc tactcctgga atccctccta tggcataccc cacccagcc tatactatac     660 cttctcttcac cagcatccca aatgggtttt acccatccaa gtccatcaac atatcaggcg     720
tggtcttgcc agatgctaag aggttccata tcaaccttcg ctgtgggggt gacattgctt     780
tccacctgaa cccccgtttc aatgagaagg ttgtggtccg aaacactcag atcaacaact     840 cctggggcc cgaggagcga agcctgcctg ggagaatgcc cttcaatcgt ggccagagtt     900
tctcagtgtg gatcttatgt gaaggtcact gcttcaaggt ggccgtggat ggtcagcata     960
tttgtgaata ttaccaccgc ctgaagaact tgccggatat caacactcta gaggtggccg    1020
gtgatatcca gctgacacac gtgcagacct aggaaggtct ctggcttagg gatgaaggct    1080
gaggaaccct acctgagtct tgtcacctcc tccctgtctc agccctgcct ccccaaatcc    1140
tgtcatcaaa gagagcctca ttggcaggag ttccaggaag gtggcattcc caattcacac    1200
cctccacaaa gggggagtcc tgggctatgg gacacatggc tgtgagccca cagtgtcagc    1260
cattgctccc aagctagtca tcttctgagg gaagtgacct ccctgggttt gccccttct    1320 ctgaccttc ccttcacccc tccaggaggg ccaccttgat gtcatcccat tggcctccag    1380
ctgacccaga atgtccacat taccttttcc ccaatctttc ccaatgccca taaaataaag    1440
aatatcaacg cttgtctaca aaaaaaaaaa aaaaaaaaaa aaaaaaaaaa aaaaaaaaaa    1500
aaaaaaaaaa aaaaaaaaaa aaaaaaaaa aaaaaaaaaa aaaaa                      1545
```

<210> SEQ ID NO 2
<211> LENGTH: 322

<212> TYPE: PRT
<213> ORGANISM: Rat

<400> SEQUENCE: 2

```
Met Ala Phe Phe Ser Thr Gln Pro Pro Tyr Met Asn Pro Val Ile Pro
 1               5                  10                  15

Phe Thr Gly Ile Ile Gln Gly Gly Leu Gln Asn Gly Leu Gln Ile Thr
             20                  25                  30

Leu Gln Gly Thr Val His Pro Phe Pro Asn Arg Ile Ala Val Asn Phe
         35                  40                  45

Gln Thr Gly Phe Ser Gly Asn Asp Ile Ala Phe His Phe Asn Pro Arg
     50                  55                  60

Phe Glu Glu Gly Gly Tyr Val Val Cys Asn Thr Lys Gln Asn Gly Lys
65                  70                  75                  80

Trp Gly Pro Glu Glu Arg Lys Met Gln Met Pro Phe Gln Lys Gly Met
                 85                  90                  95

Pro Phe Glu Leu Cys Phe Leu Val Gln Arg Ser Glu Phe Lys Val Met
            100                 105                 110

Val Asn Lys Asn Phe Phe Val Gln Tyr Ser His Arg Val Pro Tyr His
           115                 120                 125

Leu Val Asp Thr Ile Ser Val Ser Gly Cys Leu His Leu Ser Phe Ile
       130                 135                 140

Asn Phe Gln Thr Gln Gly Phe Gln Pro Ala His Gln Ala Pro Val Ala
145                 150                 155                 160

Gln Thr Ile Ile His Thr Val His Ser Ile Pro Gly Gln Met Leu Ser
                165                 170                 175

Thr Pro Gly Ile Pro Pro Met Ala Tyr Pro Thr Pro Ala Tyr Thr Ile
            180                 185                 190

Pro Phe Phe Thr Ser Ile Pro Asn Gly Phe Tyr Pro Ser Lys Ser Ile
        195                 200                 205

Asn Ile Ser Gly Val Val Leu Pro Asp Ala Lys Arg Phe His Ile Asn
    210                 215                 220

Leu Arg Cys Gly Gly Asp Ile Ala Phe His Leu Asn Pro Arg Phe Asn
225                 230                 235                 240

Glu Lys Val Val Val Arg Asn Thr Gln Ile Asn Asn Ser Trp Gly Pro
                245                 250                 255

Glu Glu Arg Ser Leu Pro Gly Arg Met Pro Phe Asn Arg Gly Gln Ser
            260                 265                 270

Phe Ser Val Trp Ile Leu Cys Glu Gly His Cys Phe Lys Val Ala Val
        275                 280                 285

Asp Gly Gln His Ile Cys Glu Tyr Tyr His Arg Leu Lys Asn Leu Pro
    290                 295                 300

Asp Ile Asn Thr Leu Glu Val Ala Gly Asp Ile Gln Leu Thr His Val
305                 310                 315                 320

Gln Thr
```

<210> SEQ ID NO 3
<211> LENGTH: 972
<212> TYPE: DNA
<213> ORGANISM: Human

<400> SEQUENCE: 3

```
atggccttca gcggttccca ggctccctac ctgagtccag ctgtcccctt ttctgggact      60
attcaaggag gtctccagga cggacttcag atcactgtca atgggaccgt tctcagctcc     120
```

-continued

```
agtggaacca ggtttgctgt gaactttcag actggcttca gtggaaatga cattgccttc      180
cacttcaacc ctcggtttga agatggaggg tacgtggtgt gcaacacgag gcagaacgga      240
agctgggggc ccgaggagag gaagacacac atgcctttcc agaagggat gcccttgac       300 ctctgcttcc tggtgcagag ctcagatttc aaggtgatgg tgaacgggat cctcttcgtg      360
cagtacttcc accgcgtgcc cttccaccgt gtggacacca tctccgtcaa tggctctgtg      420
cagctgtcct acatcagctt ccagcctccc ggcgtgtggc ctgccaaccc ggctcccatt      480
acccagacag tcatccacac agtgcagagc gcccctggac agatgttctc tactcccgcc      540
atcccaccta tgatgtaccc ccaccccgcc tatccgatgc ctttcatcac caccattctg      600
ggagggctgt acccatccaa gtccatcctc ctgtcaggca ctgtcctgcc cagtgctcag      660
aggttccaca tcaacctgtg ctctgggaac acatcgcct tccacctgaa ccccgttttt      720
gatgagaatg ctgtggtccg caacacccag atcgacaact cctggggtc tgaggagcga       780 agtctgcccc gaaaaatgcc cttcgtccgt ggccagagct tctcagtgtg atcttgtgt       840 gaagctcact gcctcaaggt ggccgtggat ggtcagcacc tgtttgaata ctaccatcgc      900
ctgaggaacc tgcccaccat caacagactg gaagtggggg gcgacatcca gctgacccat      960
gtgcagacat ag                                                          972
```

<210> SEQ ID NO 4
<211> LENGTH: 301
<212> TYPE: PRT
<213> ORGANISM: Human

<400> SEQUENCE: 4

```
Met Ala Phe Ser Gly Ser Gln Ala Pro Tyr Leu Ser Pro Ala Val Pro
 1               5                  10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
             35                  40                  45

Phe Gln Thr Gly Phe Ser Gly Asn Asp Ile Ala Phe His Phe Asn Pro
         50                  55                  60

Arg Phe Glu Asp Gly Gly Tyr Val Val Cys Asn Thr Arg Gln Asn Gly
 65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
    210                 215                 220
```

```
Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
            245                 250                 255

Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
        275                 280                 285

Val Asp Gly Gln His Leu Phe Glu Tyr Tyr His Arg Leu
    290                 295                 300

<210> SEQ ID NO 5
<211> LENGTH: 29
<212> TYPE: DNA
<213> ORGANISM: Artificial Sequence
<220> FEATURE:
<223> OTHER INFORMATION: synthetic oligonucleotide primers

<400> SEQUENCE: 5
gcgaattcgt gccctaccac ctcgtggac                              29

<210> SEQ ID NO 6
<211> LENGTH: 29
<212> TYPE: DNA
<213> ORGANISM: Artificial Sequence
<220> FEATURE:
<223> OTHER INFORMATION: synthetic oligonucleotide primers

<400> SEQUENCE: 6
gcgaattcgt atgccatagg agggattcc                              29

<210> SEQ ID NO 7
<211> LENGTH: 29
<212> TYPE: DNA
<213> ORGANISM: Artificial Sequence
<220> FEATURE:
<223> OTHER INFORMATION: synthetic oligonucleotide primers

<400> SEQUENCE: 7
gcggatccat ggctttcttc agcacccag                              29

<210> SEQ ID NO 8
<211> LENGTH: 30
<212> TYPE: DNA
<213> ORGANISM: Artificial Sequence
<220> FEATURE:
<223> OTHER INFORMATION: synthetic oligonucleotide primers

<400> SEQUENCE: 8
gcctgcagct aggtctgcac gtgtgtcagc                             30
```